United States Patent
Evans et al.

(10) Patent No.: US 9,827,409 B1
(45) Date of Patent: Nov. 28, 2017

(54) ELECTRONIC TATTOOING DEVICE AND METHOD

(71) Applicant: INLINE TATTOO MACHINES, LLC, Mooresville, NC (US)

(72) Inventors: Mark Travis Evans, Mooresville, NC (US); Grady Lee Dudding, Jr., Sailsbury, NC (US)

(73) Assignee: Inline Tattoo Machines, LLC, Mooresville, NC (US)

( * ) Notice: Subject to any disclaimer, the term of this patent is extended or adjusted under 35 U.S.C. 154(b) by 478 days.

(21) Appl. No.: 14/616,061

(22) Filed: Feb. 6, 2015

(51) Int. Cl.
*A61B 17/34* (2006.01)
*A61M 37/00* (2006.01)

(52) U.S. Cl.
CPC .............................. *A61M 37/0084* (2013.01)

(58) Field of Classification Search
CPC ................................................ A61M 37/0076
See application file for complete search history.

(56) References Cited

U.S. PATENT DOCUMENTS

| | | |
|---|---|---|
| 3,762 A | 10/1875 | Edison |
| 180,857 A | 3/1876 | Edison |
| 196,747 A | 4/1877 | Edison |
| 208,905 A | 10/1878 | Griest |
| 5,009 A | 12/1878 | Wilson |
| 464,801 A | 12/1891 | O'Reilly |
| 3,035 A | 2/1894 | MacDonald |
| 6,720 A | 5/1897 | Glorget |
| 13,539 A | 6/1899 | South |
| 768,413 A | 8/1904 | Wagner |
| 215,629 A | 7/1923 | Leresche |
| 1,724,812 A | 8/1929 | Waters |
| 1,767,469 A | 6/1930 | Metzner |
| 2,126,777 A | 8/1938 | Holt |
| 2,840,076 A | 6/1958 | Robbins |
| 3,039,467 A | 6/1962 | Stone |
| 4,031,783 A | 6/1977 | Paul |
| 4,159,659 A | 7/1979 | Nightingale |
| 4,204,438 A | 5/1980 | Binaris |
| 4,771,660 A | 9/1988 | Yacowitz |
| 4,862,772 A | 9/1989 | Piperato |

(Continued)

OTHER PUBLICATIONS

Ron Kurtus, "Alternating Current (AC) Transformers"; http://www.school-for-champions.com/science/actransormers.htm; pp. 1-7; Printed prior to Aug. 22, 2006.

(Continued)

*Primary Examiner* — Eric Rosen
*Assistant Examiner* — Son Dang
(74) *Attorney, Agent, or Firm* — Schwartz Law Firm, P.C.

(57) ABSTRACT

A tattooing device is designed for ingraining a design on the skin. The tattooing device includes an electric drive motor with a rotatable motor pin. The motor pin defines an axis of rotation. A rotatable actuator cam is operatively connected to the motor pin, and comprises a cam post axially offset from the motor pin and the axis of rotation. An elongated drive shaft is operatively connected to the cam post, such that rotation of the actuator cam effects simultaneous substantially linear reciprocating movement of the drive shaft. A needle assembly is operatively connected to the drive shaft, and adapted for carrying a pointed tattooing needle for penetrating the skin.

20 Claims, 6 Drawing Sheets

(56) References Cited

U.S. PATENT DOCUMENTS

| | | | |
|---|---|---|---|
| 4,914,988 A * | 4/1990 | Chang | A01K 11/005 606/186 |
| 5,054,339 A | 10/1991 | Yacowitz | |
| 5,279,552 A * | 1/1994 | Magnet | A61M 37/0076 604/47 |
| 5,279,570 A | 1/1994 | Dombrowski et al. | |
| 5,471,102 A | 11/1995 | Becker | |
| 5,472,449 A | 12/1995 | Chou | |
| 5,586,473 A | 12/1996 | Chou | |
| D380,046 S | 6/1997 | Domanowski | |
| 5,661,446 A | 8/1997 | Anderson et al. | |
| 5,776,158 A | 7/1998 | Chou | |
| 5,959,374 A | 9/1999 | Anderson et al. | |
| 6,013,122 A | 1/2000 | Klitzman | |
| 6,033,421 A * | 3/2000 | Theiss | A61M 37/0076 606/186 |
| 6,039,014 A | 3/2000 | Hoppie | |
| 6,040,752 A | 3/2000 | Fisher | |
| D432,653 S | 10/2000 | Paolini | |
| 6,639,496 B1 | 10/2003 | van Namen | |
| 8,562,635 B2 * | 10/2013 | Tanner | B27B 5/30 606/178 |
| 2003/0171767 A1 | 9/2003 | Koplen | |
| 2003/0195542 A1 * | 10/2003 | Lee | A61M 37/0076 606/186 |
| 2004/0143275 A1 * | 7/2004 | Chen | A61M 37/0076 606/133 |
| 2008/0055028 A1 * | 3/2008 | Mask | A61M 37/0084 335/229 |
| 2008/0306502 A1 * | 12/2008 | Lisec | A01K 11/005 606/186 |
| 2012/0123462 A1 * | 5/2012 | Lee | A61M 37/0076 606/185 |

OTHER PUBLICATIONS

"Tattoo Machine"; Tattoo Archive; http://www.tattooarchive.com/history/tattoo_machine.htm; pp. 1-4; Printed prior to Aug. 21, 2006.

"Sutherland Macdonald"; Tattoo Archive; http://www.tattooarchive.com/history/macdonald_sutherland.htm; pp. 1-3; printed prior to Aug. 21, 2006.

* cited by examiner

ELECTRONIC TATTOOING DEVICE AND METHOD

TECHNICAL FIELD AND BACKGROUND OF THE INVENTION

This invention relates broadly and generally to an electronic tattooing device and method.

SUMMARY OF EXEMPLARY EMBODIMENTS

Various exemplary embodiments of the present invention are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is also noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

According to one exemplary embodiment, the present disclosure comprises an electronic hand tool, such as a tattooing device for ingraining a design on the skin. The exemplary tattooing device includes an electric (inverted) drive motor with a rotatable motor pin. The motor pin defines an axis of rotation. A rotatable actuator cam is operatively connected to the motor pin, and comprises a cam post axially offset from the motor pin and the axis of rotation. An elongated drive shaft is operatively connected to the cam post, such that rotation of the actuator cam effects simultaneous substantially linear reciprocating movement of the drive shaft. A needle assembly is operatively connected to the drive shaft, and adapted for carrying a pointed tattooing needle for penetrating the skin. The tattooing needle reciprocates relative to the skin between needle-extended and needle-retracted positions upon reciprocating linear movement of the drive shaft.

According to another exemplary embodiment, the actuator cam defines a weight relief for balancing rotational movement of the cam relative to the motor pin.

According to another exemplary embodiment, the actuator cam defines a pin aperture receiving the motor pin of the drive motor.

According to another exemplary embodiment, the drive shaft comprises opposing proximal and distal ends, a bearing head formed at its proximal end, and an independent bearing. The bearing is located (e.g., press-fit) within the bearing head, and operatively interconnects the post of the rotatable actuator cam and the drive shaft.

According to another exemplary embodiment, a dampening spring resides adjacent the proximal end of the drive shaft, and is adapted for reducing vibration during operation of the tattooing device.

According to another exemplary embodiment, a return spring resides adjacent the distal end of the drive shaft, and bears against the drive shaft to normally urge the tattooing needle into the needle-retracted condition.

According to another exemplary embodiment, a substantially hollow open-ended, fluted, open-piece armature is carried by (secured to) the drive shaft. The armature comprises an intermediate interior partition defining an enlarged opening through which the drive shaft passes.

According to another exemplary embodiment, an internally-threaded end cap is applied to a complementary external thread formed with the distal end of the drive shaft.

According to another exemplary embodiment, at least one resilient O-ring is located adjacent the distal end of the drive shaft, and resides between the end cap and the intermediate interior partition of the armature.

According to another exemplary embodiment, the armature comprises an exterior mounting post operatively connecting the needle assembly to the drive shaft.

In yet another exemplary embodiment, the present disclosure comprises a tattooing device for ingraining a design on the skin and incorporating an multi-part assembly housing. An electric drive motor, rotatable actuator cam, and elongated drive shaft are located inside the assembly housing. The drive motor has a rotatable motor pin. The rotatable actuator cam is operatively connected to the motor pin, and comprises a cam post axially offset from the motor pin. The drive shaft is operatively connected to the cam post, such that rotation of the actuator cam effects simultaneous substantially linear reciprocating movement of the drive shaft. The drive shaft is loosely positioned sufficient to enable slight lateral shifting upon its linear reciprocating movement within the assembly housing. A needle assembly is operatively connected to the drive shaft, and is adapted for carrying a pointed tattooing needle for penetrating the skin. The tattooing needle reciprocates relative to the skin between needle-extending and needle-retracting positions upon reciprocating linear movement of the drive shaft.

According to another exemplary embodiment, the multi-part assembly housing comprises a substantially hollow body and a detachable motor mount adapted for covering the electric drive motor.

According to another exemplary embodiment, a needle tube is secured to the assembly housing and surrounds a portion of the needle assembly.

According to another exemplary embodiment, the needle tube comprises an enlarged handle.

According to another exemplary embodiment, an ink tip located at a distal end of the needle tube.

According to another exemplary embodiment, the ink tip defines an internal well and well opening for receiving a liquid tattoo ink. The term "tattoo ink" is broadly defined herein to mean any pigment combined with a carrier. Exemplary tattoo ink may be either permanent or removable (e.g., washable).

BRIEF DESCRIPTION OF THE DRAWINGS

Exemplary embodiments of the present invention will hereinafter be described in conjunction with the following drawing figures, wherein like numerals denote like elements, and wherein.

DESCRIPTION OF EXEMPLARY EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Figure 1:
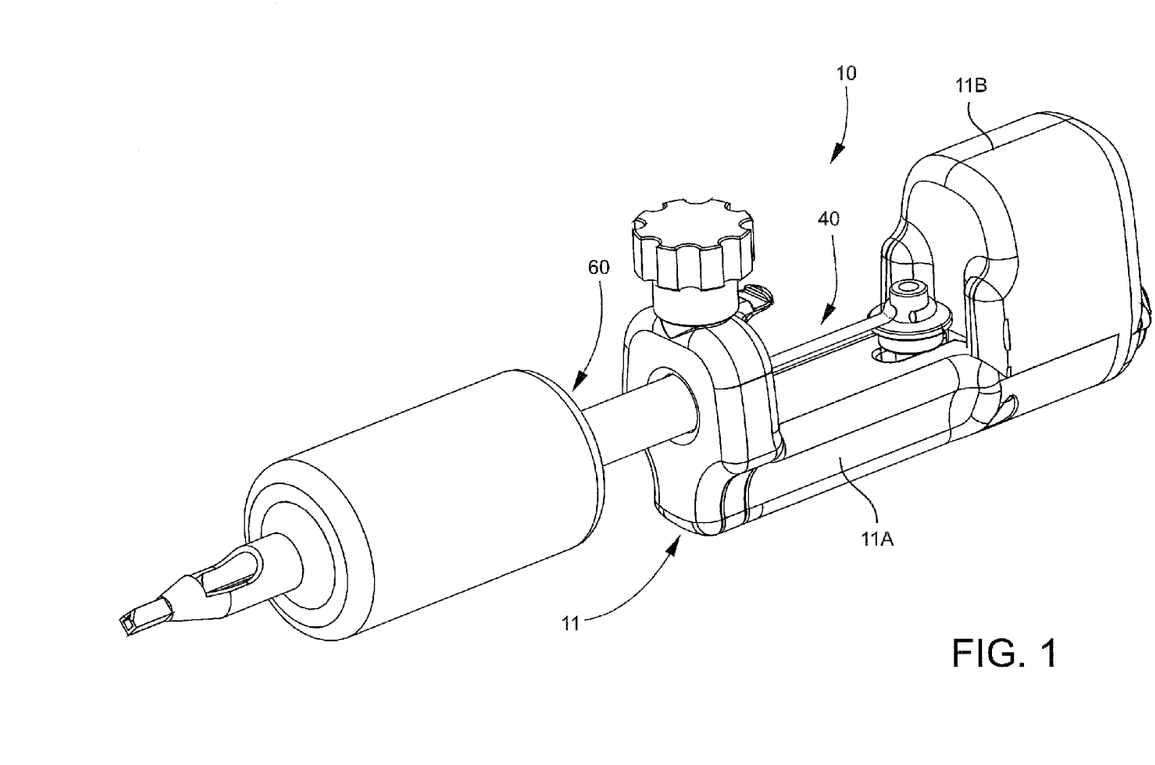
FIG. 1 is a perspective view of an electronic tattooing device according to one exemplary embodiment of the present disclosure.

Referring now specifically to the drawings, a tattooing device according to one exemplary embodiment of the present invention is illustrated in FIG. 1, and shown generally at reference numeral 10. In one implementation, the tattooing device 10 is adapted for ingraining a design on the skin using a tattooing ink. Conventional tattooing inks may comprise a pigment combined with a carrier, and may be either permanent or removable. Exemplary components and features of the present device 10 may be embodied in other hand tools or implements used in a variety of other applications, including (e.g.) use in the medical industry for dermatological injections and in the jewelry industry for setting stones.

Figure 2:
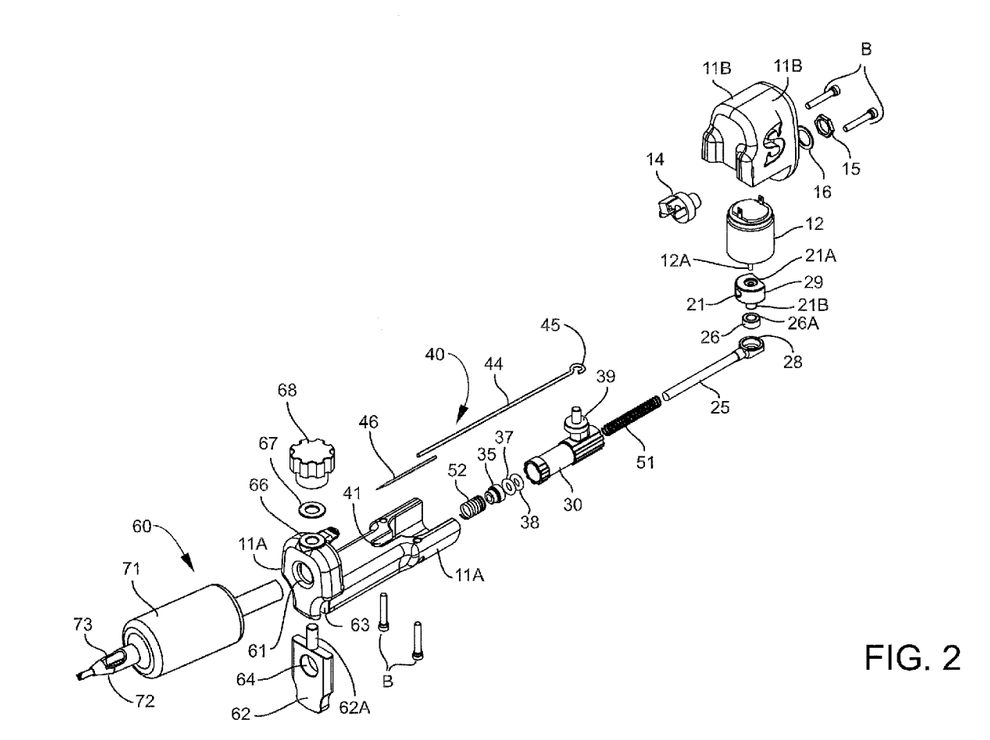
FIG. 2 is an exploded perspective view of the exemplary tattooing device.
Figure 3:
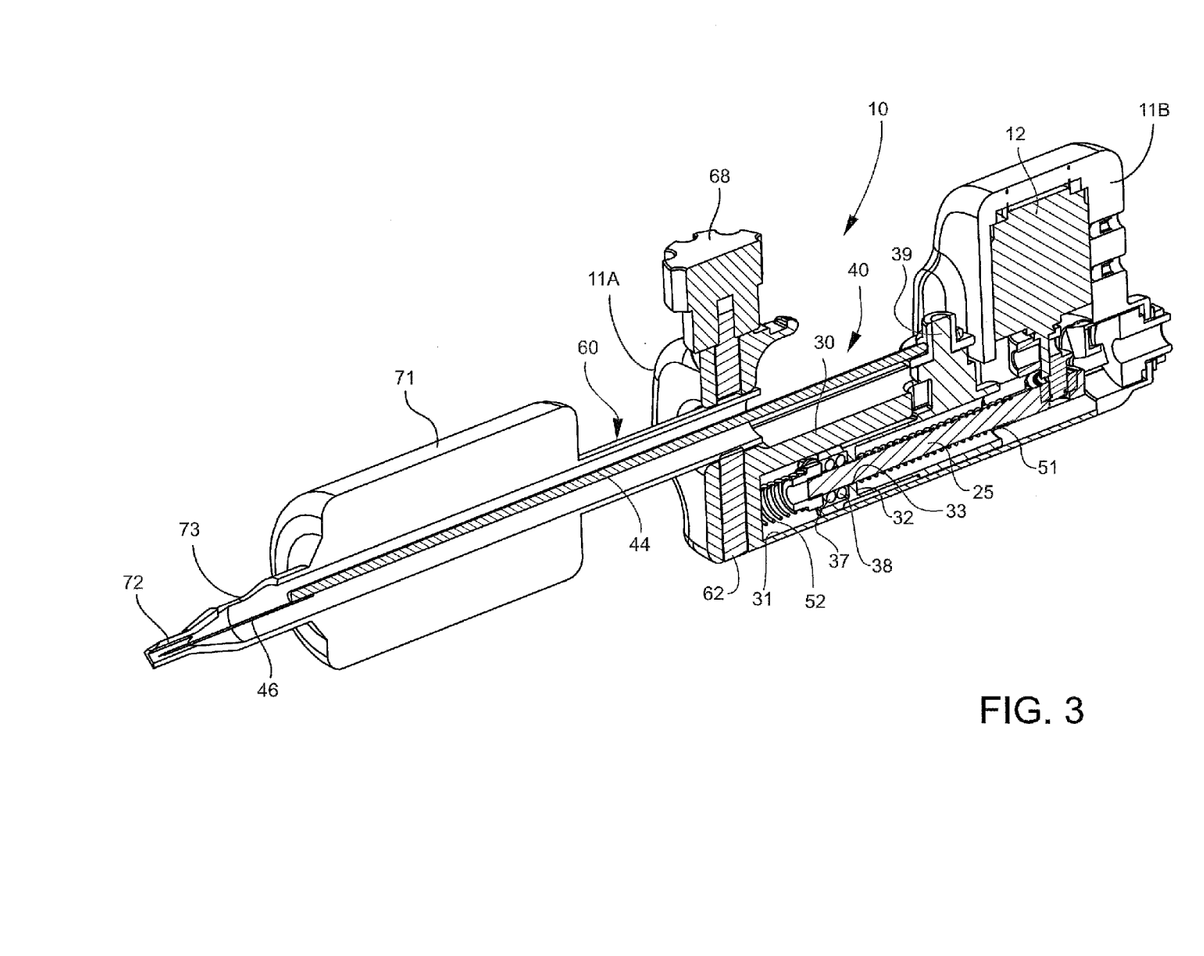
FIG. 3 is a cross-sectional view of the exemplary tattooing device.

Referring to FIGS. 1, 2, and 3, the exemplary tattooing device 10 includes a multi-piece assembly housing 11 comprising a substantially hollow body 11A and motor mount 11B. The hollow body 11A and motor mount 11B are attached together by threaded bolts "B" or other suitable hardware. The motor mount 11B covers an inverted electric motor 12 which operatively connects to an AC power supply via plug 14, plug fastener 15, washer 16, and flexible outlet cord (not shown). The device 10 may alternatively comprise one or more rechargeable batteries. The exemplary motor 12 operatively connects to a rotatable actuator cam 21 through motor pin 12A. The motor pin 12A inserts into a pin aperture 21A formed with the actuator cam 21, and functions to rotate the cam 21 relative to the motor 12 and housing 11. The actuator cam 21 operatively connects to an elongated rigid drive shaft 25 through cam post 21B and plain bearing 26. The bearing 26 is press-fit within a recessed bearing head 28 formed at a proximal end of the drive shaft 25, and defines a post aperture 26A for receiving the post 21B of the rotatable actuator cam 21. The exemplary actuator cam 21 defines a weight relief 29 for balancing rotational movement of the cam 21 relative to the motor pin 12A and drive shaft 25. The drive shaft 25 is operatively connected to the cam post 21B, such that rotation of the actuator cam 21 effects simultaneous substantially linear reciprocating movement of the drive shaft 25 relative to the housing 11.

Figure 4:
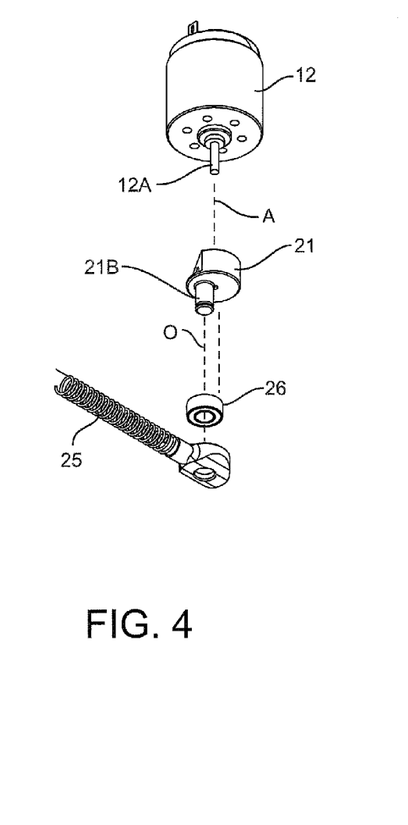
FIGS. 4 and 5 are exploded perspective views showing various internal components of the exemplary tattooing device.
Figure 5:
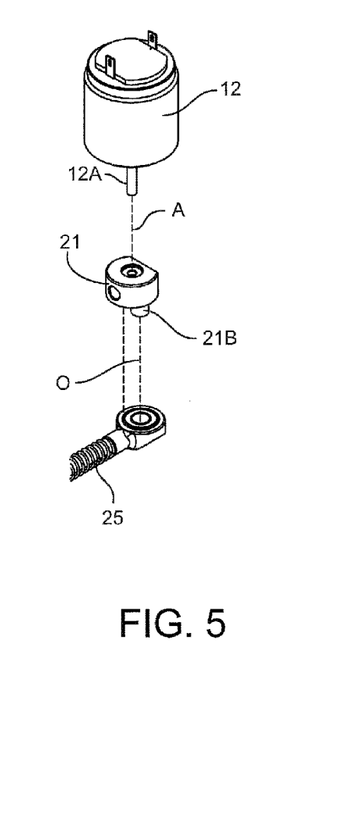
Figure 6:
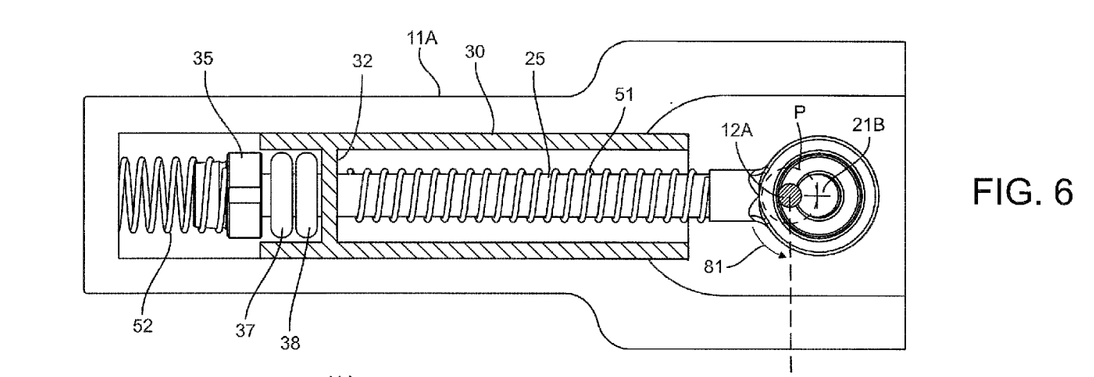
FIG. 6-9 are views demonstrating simultaneous reciprocating linear movement and lateral shifting of the drive shaft in the exemplary tattooing device.
Figure 7:
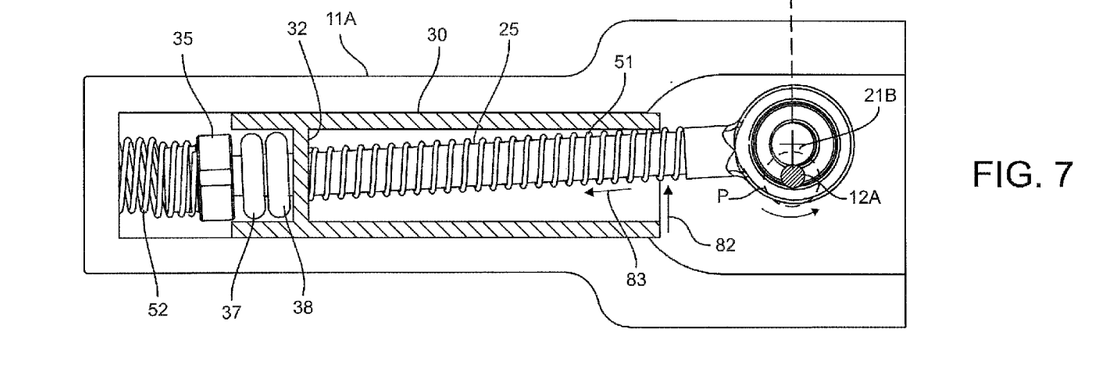
Figure 8:
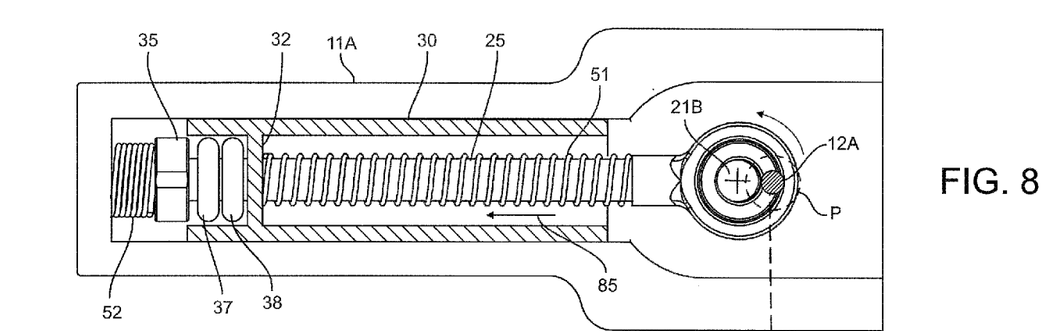
Figure 9:
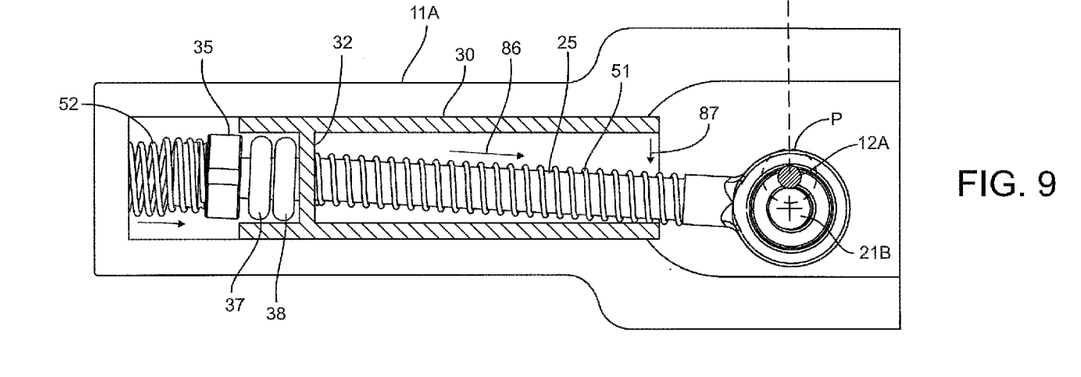

As best shown in FIGS. 4 and 5, the motor pin 12A defines a vertical axis "A" of rotation which is substantially perpendicular to the drive shaft 25 and its direction of linear movement. The cam post 21B is axially offset (e.g., by 2-5 mm), as indicated by broken line "O", from the motor pin 12A and its axis of rotation "A" such that rotation of the actuator cam 21 does not convert entirely to direct linear movement of the drive shaft 25 but instead creates slight simultaneous lateral shifting of the drive shaft 25 inside the assembly housing 11. As discussed further below, the drive shaft 25 is loosely positioned (or "floating") within the assembly housing 11 to accommodate this slight lateral shifting.

Referring again to FIGS. 2 and 3, the drive shaft 25 inserts through a fluted, hollow armature 30 comprising a substantially cylindrical interior surface 31 and an intermediate internal partition 32. The partition 32 defines an enlarged opening 33 through which a threaded distal end the drive shaft 25 extends. An internally-threaded end cap 35 or other end closure is applied to the distal end of the drive shaft 25 on a distal side of the partition 32. The end cap 35 cooperates with a pair of resilient (e.g., rubber) O-rings 37, 38 located on the drive shaft 25 adjacent the distal side of partition 32 to frictionally affix the drive shaft 25 to the armature 30. The armature 30 thereby reciprocates linearly inside the housing 11 in unison with reciprocating linear movement of the drive shaft 25 (and without lateral shifting).

The exemplary armature 30 further comprises a fixed exterior mounting post 39 which operatively connects a needle assembly 40 to the drive shaft 25, and which extend vertically through a generally U-shaped opening 41 in the body 11A of housing 11. The exemplary needle assembly 40 comprises a needle holder 44 having a hooked end 45 for attaching to the mounting post 39, and a pointed tattooing needle 46 designed for penetrating the skin. As described further below, during operation of the tattooing device 10, the tattooing needle 46 reciprocates relative to the skin between needle-extended and needle-retracted positions upon reciprocating linear movement of the drive shaft 25 and armature 30. A dampening spring 51 may be applied to the drive shaft 25 to help dampen or reduce vibration of the housing 11, and a return spring 52 may be located at the distal end of the drive shaft 25 to normally urge the tattooing needle 46 into the needle-retracted position (FIGS. 1 and 3) when power to the motor 12 is turned off.

The exemplary needle assembly 40 extends from the mounting post 39 into a needle tube 60 secured to the assembly housing 11 and passing through a tube opening 61 formed the body 11A. The needle tube 60 substantially surrounds and protects the needle assembly 40, and is secured to the assembly housing 11 by a removable vice 62. The vice 62 inserts upwardly through an underside pocket 63 formed with a distal end of the body 11A, and defines a circular opening 64 substantially corresponding to the tube opening 61. A threaded fastener post 62A is formed with the vice 62, and extends vertically through a top opening 66 of the body 11A to receive a washer 67 and complementary-threaded vice fastener 68. When the vice 62 is properly inserted into the body pocket 63, the tube opening 61 and vice opening 64 generally align in a tube-receiving position. In this position, the needle tube 60 inserts over a substantial portion of the needle assembly 40, passes through the aligned tube and vice openings 61, 64, and is clamped into a fixed condition by hand tightening the vice fastener 68.

In the exemplary embodiment shown, the needle tube 60 further comprises an enlarged cylindrical handle 71 and ink tip 72. The ink tip 72 defines an interior well and well opening 73 for receiving the tattoo ink.

Referring to FIGS. 2, 3 and 6-9, during operation of the tattooing device 10 the electric motor 12 rotates the motor pin 12A which effects simultaneous rotation of the actuator cam 21, as previously described. The cam post 21B is axially offset from the motor pin 12A and its axis of rotation, and revolves within a circular 360-degree path "P" extending around the motor pin 12A. At a 12-o'clock starting point shown in FIG. 6, the tattooing needle 46 of the needle assembly 40 (FIG. 3) is urged into the retracted position by return spring 52. As the cam post is rotated as indicated by arrow 81 from the 12-o'clock to 9-o'clock point shown in FIG. 7, the "floating" drive shaft moves simultaneously laterally and linearly as indicated by arrows 82, 83 pivoting inside the armature 30 at the enlarged opening of partition 32. The resilient O-rings accommodate lateral shifting of the drive shaft 25, while maintaining a secure (fixed) frictional connection between the drive shaft 25 and armature 30 such that the armature 30 travels linearly inside the assembly housing 11 in unison with the linear movement of the drive shaft 25. The dampening spring 51 reduces vibration created by the lateral shifting of the drive shaft 25. When rotated to the 6-o'clock position shown in FIG. 8, the cam post 21B moves the drive shaft 25 further linearly within the armature 30, as indicated by arrow 85, to locate the tattooing needle 46 in the needle-extended position. Further rotation of the cam post 21B to the 3-o'clock position, causes the drive shaft 25 to simultaneously linearly retract and shift laterally, as indicated by arrows 86 and 87, before returning to the 12-o'clock position shown in FIG. 6. In a typical application, the tattooing needle 46 travels about 2 mm between extended and retracted position.

The exemplary tattooing device 10 may utilize an operating voltage of about 15V and a current of about 0.3 A. Additionally, the tattooing device 10 may incorporate circuitry with user controls for adjusting the rate (speed) of needle reciprocation, and other standard controls for liners and shaders.

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under §112, 6th paragraph is not intended. Additionally, it is not intended that the scope of patent protection afforded the present invention be defined by reading into any claim a limitation found herein that does not explicitly appear in the claim itself.

What is claimed:

1. A tattooing device for ingraining a design on the skin, comprising:
    an electric drive motor comprising a rotatable motor pin, said motor pin defining an axis of rotation;
    a rotatable actuator cam operatively connected to said motor pin, and comprising a cam post axially offset from said motor pin and said axis of rotation;
    an elongated drive shaft operatively connected to said cam post, such that rotation of said actuator cam effects simultaneous substantially linear reciprocating movement of said drive shaft;
    a needle assembly operatively connected to said drive shaft and adapted for carrying a pointed tattooing needle for penetrating the skin, whereby the tattooing needle reciprocates relative to the skin between needle-extended and needle-retracted positions upon reciprocating linear movement of said drive shaft.

2. The tattooing device according to claim 1, wherein said actuator cam defines a weight relief for balancing rotational movement of said cam relative to said motor pin.

3. The tattooing device according to claim 1, wherein said actuator cam defines a pin aperture receiving the motor pin of said drive motor.

4. The tattooing device according to claim 1, wherein said drive shaft comprises opposing proximal and distal ends, a bearing head formed at its proximal end, and a bearing located within said bearing head and operatively interconnecting the post of said rotatable actuator cam and said drive shaft.

5. The tattooing device according to claim 4, and comprising a dampening spring adjacent the proximal end of said drive shaft, and adapted for reducing vibration during operation of said tattooing device.

6. The tattooing device according to claim 4, and comprising a return spring adjacent the distal end of said drive shaft, and bearing against said drive shaft to normally urge the tattooing needle into the needle-retracted condition.

7. The tattooing device according to claim 4, and comprising a substantially hollow open-ended armature carried by said drive shaft, and comprising an intermediate interior partition defining an enlarged opening through which said drive shaft passes.

8. The tattooing device according to claim 7, and comprising an internally-threaded end cap applied to a complementary external thread formed with the distal end of said drive shaft.

9. The tattooing device according to claim 8, and comprising at least one O-ring located adjacent the distal end of said drive shaft, and residing between said end cap and the intermediate interior partition of said armature.

10. The tattooing device according to claim 7, wherein said armature comprises an exterior mounting post operatively connecting said needle assembly to said drive shaft.

11. A tattooing device for ingraining a design on the skin, comprising:
   an assembly housing;
   an electric drive motor inside said assembly housing and comprising a rotatable motor pin;
   a rotatable actuator cam inside said assembly housing and operatively connected to said motor pin, and said actuator cam comprising a cam post axially offset from said motor pin;
   an elongated drive shaft inside said assembly housing and operatively connected to said cam post, such that rotation of said actuator cam effects simultaneous substantially linear reciprocating movement of said drive shaft, and said drive shaft being loosely positioned sufficient to enable slight lateral shifting upon its linear reciprocating movement within said assembly housing;
   a needle assembly operatively connected to said drive shaft, and adapted for carrying a pointed tattooing needle for penetrating the skin, whereby the tattooing needle reciprocates relative to the skin between needle-extending and needle-retracting positions upon reciprocating linear movement of said drive shaft.

12. The tattooing device according to claim 11, wherein said actuator cam defines a weight relief for balancing rotational movement of said cam relative to said motor pin.

13. The tattooing device according to claim 11, wherein said drive shaft comprises opposing proximal and distal ends, a bearing head formed at its proximal end, and a bearing located within said bearing head and operatively interconnecting the post of said rotatable actuator cam and said drive shaft.

14. The tattooing device according to claim 13, and comprising a dampening spring adjacent the proximal end of said drive shaft, and adapted for reducing vibration during operation of said tattooing device.

15. The tattooing device according to claim 13, and comprising a return spring adjacent the distal end of said drive shaft, and bearing on said drive shaft to normally urge the tattooing needle into the needle-retracted condition.

16. The tattooing device according to claim 11, wherein said assembly housing comprises a substantially hollow body and a detachable motor mount adapted for covering said electric drive motor.

17. The tattooing device according to claim 11, and comprising a needle tube secured to said assembly housing and surrounding a portion of said needle assembly.

18. The tattooing device according to claim 17, wherein said needle tube comprises an enlarged handle.

19. The tattooing device according to claim 18, and comprising an ink tip located at a distal end of said needle tube.

20. The tattooing device according to claim 19, wherein said ink tip defines a well opening for receiving a liquid tattoo ink.

* * * * *